United States Patent [19]

Williams et al.

[11] 4,379,085
[45] Apr. 5, 1983

[54] HEAT STABILIZATION OF PLASMA PROTEINS

[75] Inventors: Craigenne A. Williams; Milan Wickerhauser, both of Bethesda, Md.

[73] Assignee: American National Red Cross, Washington, D.C.

[21] Appl. No.: 378,229

[22] Filed: May 14, 1982

[51] Int. Cl.$^3$ ................................................ C07G 7/00
[52] U.S. Cl. ................................. 260/112 B; 424/101
[58] Field of Search ...................... 260/112 B; 424/101

[56] References Cited

U.S. PATENT DOCUMENTS 2,867,567  1/1959  Bidwell .......................... 260/112 BX
4,170,590  10/1979  Stephan et al. .................. 260/112 B

OTHER PUBLICATIONS

Wickerhauser, et al., "Development of Large Scale Fractionation Methods", *Vox Sang.*, 36:281–293, (1979).
Wickerhauser, et al., "Antithrombin III Concentrates for Clinical Use: The Effects of Pasteurization and Freeze Drying", Abs. #35.
Busby, et al., "Thermal Denaturation of Antithrombin III", *Journal of Biological Chemistry*, vol. 256, No. 23, 12140–12147, (1981).

*Primary Examiner*—Howard E. Schain
*Attorney, Agent, or Firm*—Holman & Stern

[57] ABSTRACT

A method for the heat stabilization of a plasma protein such as C1-INA or Factor IX comprising heating the protein in an aqueous medium in the presence of potassium or ammonium citrate in an amount of from in excess of 2.0 M to saturation of the medium. The method is particularly applicable to the stabilization of plasma proteins against thermal denaturation during pasteurization.

10 Claims, 2 Drawing Figures

HEAT STABILIZATION OF PLASMA PROTEINS

BACKGROUND OF THE INVENTION

The complement system, an immune response effector mechanism, comprises a set of proteins activated by the presence of antibody/antigen complexes in the host to initiate a cascade of proteolytic cleavage and protein binding events which promote elimination of the antigens from the host. Physiological responses to activation of the complement system include acute local inflammation, dilation of blood vessels, and transudation of fluid into interstitial spaces.

The human complement system includes component C1, a complex of protein subcomponents including serine esterase (C1-esterase), which participates in the proteolytic cleavage sequence of the mechanism. Activation of the C1 component of the complement system and enzymatic activity of C1-esterase is regulated by a serum inhibitor, C1-inactivator (C1-inhibitor) which controls the activity of C1-esterase. A functional deficiency of this inactivator protein results in a condition termed hereditary angioneurotic edema, caused by repeated unchecked activation of the complement system and symptomized by recurrent episodes of local acute inflammation at sites of activation. The accompanying vessel dilation and transudation of fluid into tissue spaces can cause suffocation if activation occurs at sensitive sites in the upper respiratory tract.

Acute attacks of swelling in hereditary angioedema are successfully treated by the administration of functionally active serum C1-inactivator (C1-INA), preferably as a concentrated plasma fraction. Plasma concentrates of C1-INA currently used in clinical replacement therapy have been implicated as a cause of transfusion hepatitis, however. Accordingly, research efforts have been directed to methods for preparing C1-INA concentrates which provide a high yield of biologically active C1-INA and which also provide a product concentrate having minimized potential for transmitting hepatitis B virus (herein also referred to as HBV).

Current methods for purification of C1-INA typically include the step of polyethylene glycol (PEG) precipitation, which removes extraneous complement system proteins; the product C1-INA fraction, however, retains potential for viral infection. The classic pasteurization approach to inactivation of plasma HBV, successfully employed in providing safe clinical serum albumin, has not heretofore been useful in providing safe clinical C1-INA, since this protein denatures under the required pasteurization conditions. Attempts to improve the heat stability of C1-INA have not significantly improved recovery of active material. The use of N-acetyltryptophanate, sodium caprylate, and sodium citrate, successfully employed as heat stabilizers in the pasteurization of the plasma proteins albumin and antithrombin III, respectively, have not provided adequate protection for C1-INA during pasteurization. Losses in C1-INA activity attributable to heat denaturation during pasteurization in the presence of sodium citrate, for example, typically exceed 25%; in addition to lacking cost-effectiveness, the large amount of protein denatured and subsequently infused into patients can adversely affect continued efficacy of the treatment. Heat denaturation has been encountered in the pasteurization of other plasma proteins such as Factor IX, used for replacement therapy in the treatment of hemophilia B.

SUMMARY OF THE INVENTION

The invention encompasses a method for the heat stabilization of a plasma protein comprising heating the protein in the presence of potassium citrate or ammonium citrate. In particular, the invention includes a method for the pasteurization of a Factor IX or C1-INA plasma concentrate in the presence of ammonium or potassium citrate. The invention further includes a method for the preparation of a pasteurized C1-INA or Factor IX concentrate from plasma or a fraction thereof comprising partially purifying C1-INA or Factor IX according to known protein separation techniques and heating the resultant partially purified fraction in the presence of potassium or ammonium citrate under conventional time and temperature pasteurizing conditions.

The methods of the invention successfully stabilize both C1-INA and Factor IX against heat denaturation, with up to 100% retained activity, and further may eliminate or substantially reduce the risk of HBV contamination of the pasteurized protein. Additionally, the methods of the invention are also applicable to the heat stabilization of other heat-sensitive plasma proteins and the prevention of the thermal denaturation of these proteins under pasteurization conditions; exemplary of such plasma proteins which can be heat-stabilized according to the present invention are antithrombin III, Factor X, and Factor II.

DETAILED DESCRIPTION OF THE INVENTION

Figure 1:
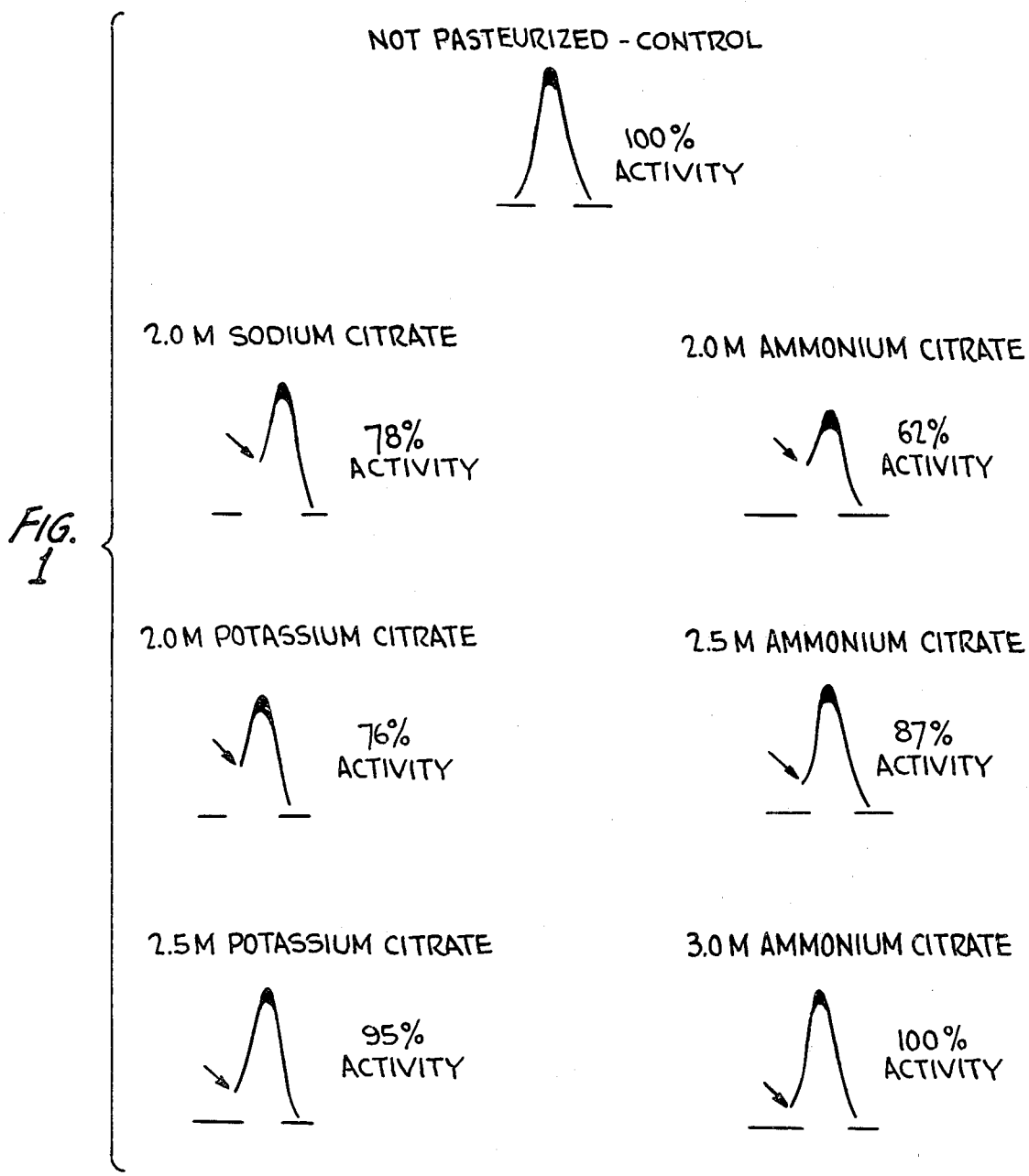
FIG. 1 shows the precipitation curves obtained by immunoelectrophoresis as well as the specific activities of C1-INA pasteurized according to the process of the present invention.

According to the invention, plasma proteins are stabilized against thermal denaturation by the presence of potassium or ammonium citrate in concentrations of from in excess of 2.0 M to saturation, preferably from about 2.5 M to saturation. Typically, a high molar citrate solution and/or citrate powder is added to an aqueous protein suspension in amounts sufficient to provide a citrate concentration in excess of 2.0 M; the pH of the solution is then preferably adjusted to about neutral with citric acid. Alternatively, a saturated or supersaturated solution of the citrate, is adjusted to a pH of about neutral with citric acid, and the protein sample added to the citrate to give the desired citrate concentration.

While suspension concentrations of ammonium citrate (Am-Cit) of about 3.0 M are conveniently obtained by the addition of saturated solutions of ammonium citrate (3.6 M at room temperature) to the protein suspension, suspension concentrations of potassium citrate (K-Cit) of about 3.0 M require the use of a combination of citrate powder and high molar citrate solutions, or a supersaturated citrate solution, since the saturation concentration of potassium citrate at room temperature is 3.0 M. Thus, for example, a 3.0 M suspension concentration of potassium citrate can be achieved by the addition of about 5 volumes of 3.0 M K-Cit solution to about 1 volume of the protein suspension to give a K-Cit concentration of about 2.5 M, followed by the addition of K-Cit powder to give a suspension concentration of 3.0 M K-Cit. This sequence results in an acceptably low rise in pH, generally less than 8, and requires only sufficient citric acid to lower the pH of the suspension to about neutral, preferably from about 7.0 to 7.5. In an alternate example, 3.3 M tripotassium citrate is added to a protein sample in proportions sufficient to give a K-Cit concentration in the sample of about 3.0 M. The sample is then adjusted to about neutral with citric acid.

The invention is particularly applicable to pasteurization techniques directed toward the inactivation of hepatitis viral contaminants associated with plasma proteins, since the presence of ammonium or potassium citrate in this concentration prevents significant loss of biological activity of these proteins during pasteurization and may permit large-scale preparation of a clinically safe product.

The method of the invention is applicable to a variety of plasma proteins including antithrombin III (AT III) and Factors X and II, but is particularly useful with the plasma proteins C1-INA and Factor IX, which are not effectively stabilized against thermal denaturation during pasteurization by known heat stabilizers. Both C1-INA and Factor IX can be stabilized according to the invention so that under typical pasteurization conditions, for example, 60° C. for 10 h, substantially complete biological activity is retained, with expected concomitant inactivation of associated (HBV) factors.

In the pasteurization method of the invention, a plasma protein concentrate is pasteurized at from 60° C. ($\pm\frac{1}{2}$° C.) for at least 10 hrs in the presence of potassium or ammonium citrate in concentrations of from in excess of 2.0 M to saturation, preferably at a pH of about neutral. In an exemplary embodiment of the invention, a pasteurized C1-INA plasma concentrate is prepared from a plasma cryosupernatant by first employing conventional protein separation techniques such as ion-exchange chromatography and PEG (polyethylene glycol) precipitation. The product C1-INA fraction is advantageously concentrated and then pasteurized in the presence of potassium or ammonium citrate in an amount providing a citrate concentration in the C1-INA fraction of from in excess of 2.0 M to saturation. Since the effectiveness of the potassium and ammonium citrate stabilizers of the invention tends to increase with increasing concentrations, in most applications, the citrate concentration of the C1-INA concentrate is preferably at or near the saturation point, in order to retain maximum biological activity of C1-INA. At the preferred temperature range of about 25° C. for addition of the stabilizer to the concentrates, saturation and concentration for potassium citrate is about 3.0 M, and for ammonium citrate, about 3.6 M. The stabilizers may be added to the concentrates at somewhat higher temperatures, in which case the saturation concentrations will be higher. For clinical use, the pasteurized C1-INA concentrate is then desalted, filtered and lyophilized according to known methods. Pasteurized Factor IX plasma concentrate is prepared by comparable purification techniques and pasteurization in the presence of potassium or ammonium citrate in the specified concentrations.

The purified C1-INA plasma concentrate for pasteurization according to the invention is prepared according to known methods, for example those described in detail in *An Improved Method For Preparation Of C1-Inactivator Concentrate*, Wickerhauser, presented as Poster No. 802, Joint Congress of the International Societies of Hematology and Blood Transfusion, Montreal, 1980. While immunoadsorption is not excluded as a separation technique in the present invention, a clinically suitable concentrate can be prepared by the use of nonspecific protein separation procedures, followed by pasteurization. Typically, a combination of PEG precipitation and ion-exchange chromatography on, for example, DEAE-Sephadex and CM-Sephadex, is employed to reduce the protein complexity of the starting plasma fraction, usually a plasma cryosupernatant.

It is highly desirable to employ a PEG precipitation step in the C1-INA purification procedure, since PEG precipitation provides a supernatant containing C1-INA from which complement components C1-C5 have been removed. Preferably, a C1-INA fraction is first extracted from plasma cryosupernatant on DEAE-Sephadex followed by precipitation of impurities in the eluate with 20% PEG 4000, and adsorption and elution of the PEG supernatant on CM-Sephadex; this sequence simplifies the use of the remaining plasma for ethanol fractionation and recovery of clinical albumin. However, if recovery of albumin is not of interest, PEG can be added directly to the cryosupernatant, followed by sequential ion-exchange chromatography of the PEG supernatant.

The purified C1-INA fraction obtained by the purification steps employed is then desirably concentrated by, for example, ultrafiltration in a Pellicon UF membrane system for large batches, or by ammonium sulfate precipitation and desalting on Sephadex G-50 for small batches. The resultant concentrate is then pasteurized according to the process of the invention and desalted, filtered, and lyophilized to provide a C1-INA concentrate final product of intermediate purity, typically 60% to 150% purification over plasma at a yield of about 14% to 45% for large-scale procedures. If desired, the final product of intermediate purity can be further purified, as by column chromatography on hydroxylapatite, to provide a high purity final product, typically up to a 400 fold increase in purification over plasma with a yield of about 6% to 17% for large-scale procedures.

EXAMPLES

I. Preparation of Purified C1-INA Concentrate

Example 1

After removal of cryoprecipitate for recovery of antihemophilic factor (AHF) cryosupernatant obtained from fresh frozen plasma was batch-adsorbed on DEAE-Sephadex (6 g/l) equilibrated in citrate saline (CS); the unadsorbed proteins were removed for ethanol fractionation and the DEAE cake washed with CS buffer (0.5 plasma volume), followed by elution with 2 M NaCl in 0.03 M citrate, pH 6.8 (0.2 plasma volume). The eluate was concentrated to 0.1 plasma volume, equilibrated with 0.06 M citrate phosphate (CP) buffer, pH 7.0, and precipitated with 20% PEG 4000. After centrifugation, the PEG supernatant was diluted with an equal volume of water and adjusted to pH 6.0, followed by adsorption on CM-Sephadex (6 g/l starting plasma), equilibrated in 0.03 M CP, pH 6.0. The CM cake was washed with the same buffer and eluted with 2 M NaCl in 0.03 M CP, pH 7.3. The eluate was then concentrated to 0.02 plasma volume, and equilibrated with CS buffer by ultrafiltration. The product was then sterile filtered, dispensed and lyophilized to give an intermediate purity C1-INA product concentrate. Recovery of C1-INA was 29.4% of the C1-INA present in the starting plasma with 91.6 fold purification. Complement components C1-C5 were undetectable by the Ouchterlony technique.

Example 2

Cryosupernatant obtained according to Example 1 was treated with solid PEG 4000 in the amount of 40 g/l at 5° C. After stirring for 1 hr, a first fraction was removed by centrifugation, and an additional 60 g/l PEG added to the supernatant to a final concentration of about 10%, based on the original volume of cryosupernatant. Prothrombin complex (PTC) was extracted from the 10% PEG supernatant by batchwise adsorption on DEAE-cellulose, and an additional 100 g/l of PEG were added to the eluate to a concentration of about 20%, again based on the original volume of cryosupernatant. The 20% PEG precipitate was separated by centrifugation and discarded, and the 20% PEG supernatant was batch adsorbed on DEAE-Sephadex (6.5 g/l starting plasma), preswollen in citrate saline (CS). After removal of unadsorbed proteins, the product DEAE cake was washed with 0.15 M NaCl, followed by elution with 2 M NaCl in 0.03 M citrate at pH 6.8 (200 ml/l starting plasma). The DEAE eluate was concentrated on a pellicon UF system, and equilibrated in 0.03 M citrate-phosphate buffer (CP) at pH 6.1, followed by adsorption with CM-Sephadex (6 g/l starting plasma) preswollen in 0.03 M CP, pH 6.0. The CM-Sephadex cake was washed with the same buffer and eluated with 1 M NaCl in CP buffer, pH 6.8 (200 ml/l starting plasma). The CM eluate was then concentrated, equilibrated in CS, sterile filtered, filled, and lyophilized to give a product C1-INA concentrate of intermediate purity.

Example 3

The procedure of Example 2 was followed, except the concentrated CM eluate was equilibrated in 10 mM $KHPO_4$ at pH 7.0 and chromatographed on OH-Apatite (4 g/l starting plasma). NaCl was added to isotonicity to the OH-Apatite unadsorbed fraction, and the isotonic product sterile filtered, filled and lyophilized to give a product C1-INA concentrate of high purity.

Example 4

Alternatively, the concentrated CM eluate of Example 1 is equilibrated and chromatographed according to Example 3, with addition of NaCl to isotonicity followed by sterile filtering, filling and lyophilization to give a high purity C1-INA product concentrate.

II. Pasteurization of C1-INA Concentrate

Example 5

An intermediate purity C1-INA concentrate obtained according to the procedure of Example 1 was pasteurized in the presence of 3 M potassium citrate (K-Cit) as follows:

(a) 5 g of C1-INA concentrate was reconstituted with 50 ml $H_2O$. The sample was stored at 5° C. for 7 h, followed by addition of 250 ml 3 M K-Cit (pH 7.3) and 80.5 g K-Cit powder (1.61 g/ml) to a final concentration of 3.0 M K-Cit. The addition of stabilizer caused precipitation of the protein. The pH of the resulting turbid suspension (pH 7.7) was then slowly adjusted to 7.45 with 3 M citric acid. The stabilized suspension was then pasteurized by heating for 10 h at 60° C.±0.1° C. The solid cake of precipitated proteins formed on top of the reaction mixture was disturbed and resuspended, and was reformed by centrifugation for 20 min at 5000 rpm at room temperature. The clear supernatant was carefully syphoned from the centrifuge cups. 210 ml of clear supernatant and about 200 ml of slurry were obtained. The supernate was found to be free of proteins and was later discarded.

The 200 ml of slurry was diluted to 600 ml with $H_2O$, dropping the pH to 6.25. 50 ml of 0.1 N NaOH and 400 ml 0.2 M $Na_2HPO_4$ were added to a final volume of 1050 ml and a pH of 6.4. The solution was stored overnight at 5° C. and then clarified through MILLIPORE filters with a final pore size of 0.22μ, obtaining a final volume of 960 ml. The clarified product was concentrated and diafiltered on a Pellicon ultrafiltration system, using PTGC membranes, (10,000 dalton nominal pore size) to about 200 ml (high circulation for 3 hrs at a flow rate of about 1350 ml/hr). The resultant concentrate was then diafiltered (DF) against 2520 ml phosphate saline buffer (PBS) containing 10 mM $NaPO_4$ + 150 mM NaCl, pH 7.25. Aliquots of the diafiltrate were taken every 600 ml to monitor removal of the potassium using a flame photometer. The potassium concentration dropped to a clinically safe range of less than 1 meq. after 1880 ml diafiltration buffer was used. The C1-INA containing retentate was then concentrated down to 160 ml, taken out of the Pellicon system, diluted to 200 ml with the PBS buffer, dispensed in 20 ml fills in 50 ml vials, frozen in liquid nitrogen, and lyophilized. The lyophilization cycle was 5 days and 16 hours. The product temperature during the primary (sublimation) phase was maintained at −35° C., and during the secondary phase at +20°−21° C. The pasteurized C1-INA was assayed for biologic and antigenic activity, protein concentration, and characterized by crossed immunoelectrophoresis in heparinized agarose gel.

The results, as shown in Table I, indicate that the pasteurization step in the presence of 3.0 M K-Cit resulted in about a 10% total protein loss, but no drop in specific activity and minimal changes in the crossed immunoelectrophoretic analysis (see FIG. 1).

(b) Before discarding the 210 ml clear supernate, a 10 ml aliquot was saved frozen and the remaining 200 ml was diluted to 1000 ml with PBS buffer. The diluted supernate was clarified on MILLIPORE membranes (0.22μ pore size), concentrated on 2 packs of the Pellicon PTGC membrane to 150 ml, and diafiltered against 1840 ml PBS buffer. After removal from the Pellicon system, the solution was diluted to 200 ml with the PBS buffer, dispensed and frozen. It was tested for proteins by taking 3 ml of the solution and adding 2 ml of 50% solution of trichloroacetic acid (TCA) solution. No precipitate developed, indicating the absence of any detectable protein.

TABLE I

| | | | | (3.0M K-CITRATE) | | | | |
|---|---|---|---|---|---|---|---|---|
| | Volume | Protein | Antigen | Activity | | RECOVERY RATIO | | |
| Step | ml | mg/ml | C1-INA | PE/ml | AG | ACT | PROT | ACT/AG | ACT/PRO |
| Before Pasteurization* | 200 | 22.7 | 20.75 | 25.0** | 100 | 100 | 100 | 1.20 | 1.10 |

TABLE I-continued

|  | Volume | Protein | Antigen | Activity | RECOVERY RATIO (3.0M K-CITRATE) | | | | |
|---|---|---|---|---|---|---|---|---|---|
| Step | ml | mg/ml | Cl-INA | PE/ml | AG | ACT | PROT | ACT/AG | ACT/PRO |
| After Pasteurization | 200 | 20.9 | 19.0 | 22.63 | 91.6 | 90.5 | 92.1 | 1.19 | 1.08 |
| After Pasteurization and Lyoph.+ | 200 | 20.2 | 18.4 | 22.37 | 88.7 | 89.5 | 89.0 | 1.20 | 1.11 |

**Assigned Value
*Control Sample
+Lyophilized Sample from Example 1

Example 6

An intermediate purity C1-INA concentrate obtained according to the procedure of Example 1 was pasteurized in the presence of 2.0 M Na-Cit, 2.0 M K-Cit, 2.5 M K-Cit, 3.0 M K-Cit, 2.0 M ammonium citrate (Am-Cit), 2.5 M Am-Cit, and 3.0 M Am-Cit, following the procedure of Example 5, except employing 3.6 M Am-Cit where relevant.

The heat stability of C1-INA under pasteurizing conditions was assessed by immunoelectrophoresis of the pasteurizates in heparinized agar gel employing a barbital buffer, pH 8.6 (I=0.075 in chambers, 0.025 in gel). Samples were diluted to about 1.0 PE/ml, in 1:3 citrate saline (CS). An unpasteurized control sample was diluted in CS.

Operating conditions were as follows:
$1^{st}$ Dimension: (16.6 $\mu$/ml heparin) 178V, for 2 h.
$2^{nd}$ Dimension: (3% Ab to C1-INA) 148V, overnight.
Temperatures: 16° C. cooling under plate, 3° C. cooling in condensation coil, 26° C. ambient temperature.

The results showing retained immunological reactivity of the pasteurizates as compared to the control sample, are shown in FIG. 1.

The biologic activity remaining is given as a percent of the specific activity of the unpasteurized control. The biologic activity was determined by the method of Levy and Lepow, *Proc. Soc. Exp. Biol. Med.*, 101:608, 1959.

III. Preparation Of Purified Factor IX Concentrate

Example 7

After removal of cryoprecipitate for recovery of AHF, cryoprecipitate supernatant plasma was adsorbed into DEAE-Sephadex A50 (70 mM Na-Citrate, pH 6, 1.7 g dry weight/liter plasma); the A50 cake was washed with 70 mM Na-Citrate, pH 6, and eluted with 200 mM Na-Citrate, pH 6. The eluted Factor IX complex (vitamin K-dependent clotting Factors II, IX, X, and protein C) were clarified and concentrated (x15) by diafiltration against 0.15 M NaCl in 20 mM Citrate, pH 6, followed by adsorption on sulfated dextran, according to the method of Miletich, et al., *Analytical Biochemistry*, 105:304–310 (1980). Stepwise elution with NaCl in increasing concentration (0.15 M, 0.25 M, 0.45 M, and 0.80 M) successively separated prothrombin, Factor X and Protein C, and Factor IX. The resultant Factor IX concentrate was essentially free of Factor X and prothrombin, and had a specific activity of about 17.6 units Factor IX/mg protein.

Either dextran-sulfate-Sepharose or heparin-Sepharose may be used instead of sulfated dextran. An elaboration on methods of preparation of Factor IX and related concentrates is set forth by Doris Menache, *Prothrombin Complex Concentrates: Clinical Use*, Ann. N.Y. Acad. Sci., 370:747–756 (1981), and in a copending patent application entitled "Plasma Protein Concentrates Of Reduced Thrombogenicity And Their Use In Clinical Replacement Therapy", filed on Apr. 28, 1982.

IV. Pasteurization Of A Factor IX Concentrate

Example 8

A high purity concentrate of Factor IX obtained as described in Example 7 as pasteurized in the presence of 3.0 M K-Cit according to the method of Example 6. The thermal denaturation of the pasteurized sample as compared to an unpasteurized control sample was monitored by ANS fluorescence according to the process described by Busby, et al., *Thermal Denaturation of Antithrombin III*, J. Bio. Chem., 256:12140–12147, 1981.

The monitored samples were constituted as follows:

|  | Factor IX | 0.02M KPO$_4$, pH 7.35 | | |
|---|---|---|---|---|
|  |  | 0.15M NaCl | 2mM ANS | 3.5M K-Cit |
| 1. Control Sample | 10λ | 86.7λ | 3.3λ | 0 |
| 2. Test Sample (3.0M citrate concentration) | 10λ | 1.0λ | 3.3λ | 85.7λ |

Figure 2:
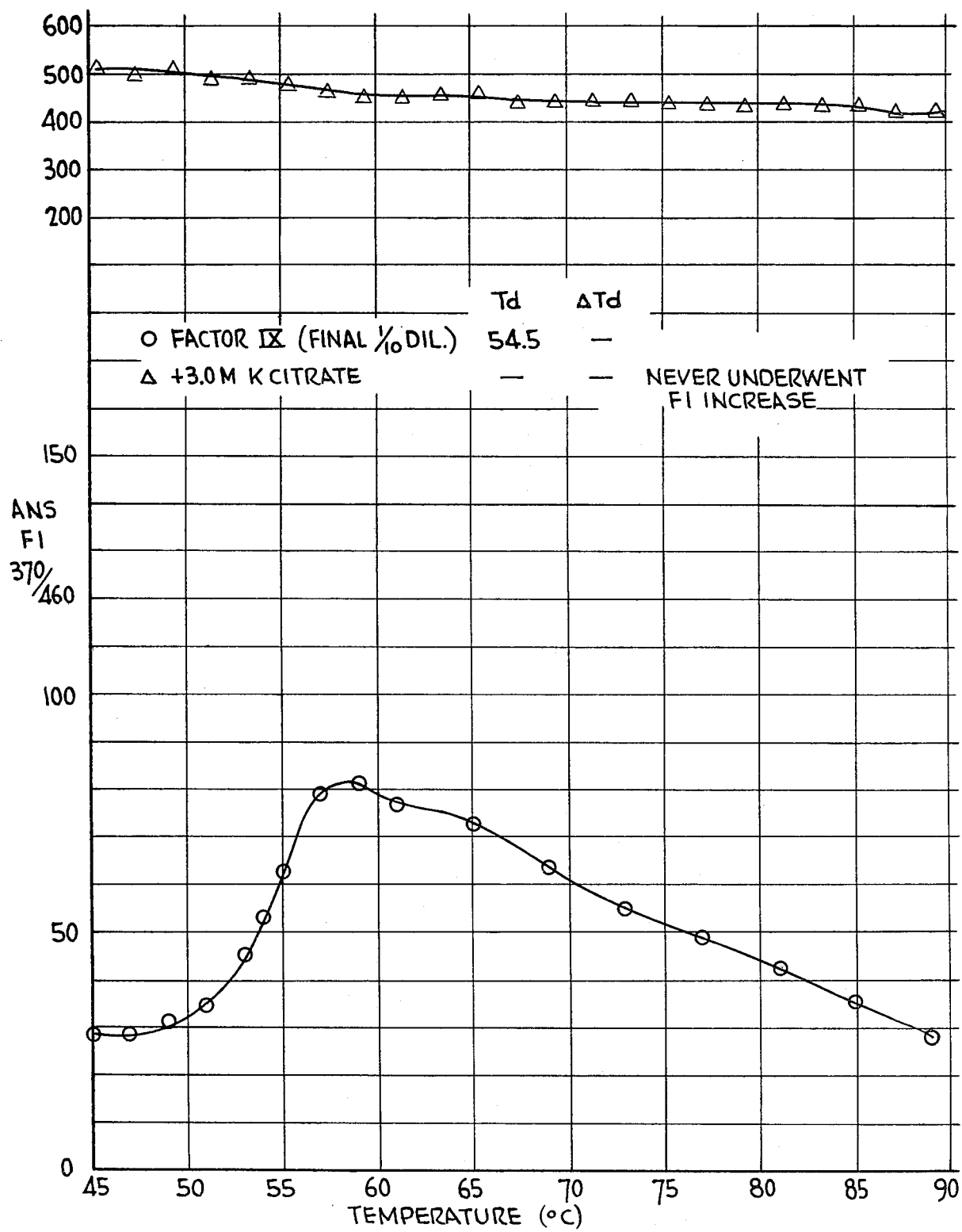
FIG. 2 is a graph comprising the thermal denaturation curves of Factor IX, and Factor IX stabilized according to the process of the present invention.

The data obtained, comprising fluorescence emission measurements, was plotted as a function of increased sample temperature. The resultant thermal denaturation curve, shown in FIG. 2, reflects the thermal stability of the test sample as compared to the thermal denaturation temperature ($T_d$) of the control sample, 54.5° C.

Example 9

Five (5) samples of a Factor IX concentrate similar to that of Example 8 were pasteurized at 60° C. for 10 hrs in the following formulations:

|  | Sample 1 | Sample 2 | Sample 3 | Sample 4 | Sample 5 (buffer control) |
|---|---|---|---|---|---|
| Salt (conc.) | 3M K-Cit | 1.8M Tricarballylate (Potassium Salt) | 2.0M K-Tricarballylate and 1.2M K-Gluconate | 1.8M K-Cit 1.8M K-Gluconate |  |

-continued

|  | Sample 1 | Sample 2 | Sample 3 | Sample 4 | Sample 5 (buffer control) |
|---|---|---|---|---|---|
| Factor IX ($\mu$/ml) | 2.8 | 3.9 | 2.6 | 2.3 | 9.9 |
| Volume (ml) | 7.1 | 7.3 | 9.0 | 9.1 | 1.9 |
| Total Factor IX Units | 19.9 | 28.5 | 23.4 | 20.9 | 18.8 |

The pasteurized samples were dialyzed into citrated saline (0.02 M Na Citrate, 0.15 M NaCl, pH 6, +4° C.) to reduce the citrate concentration of the samples and reduce inhibition to the clotting assay. The dialysate was changed three (3) times, introducing 1800 to 2000 ml of fresh, cold 20 mM Citrate (pH 6, 0.15 M NaCl) at each change. Total dialyzation time was 22 hrs.

The clotting activity of the dialyzed, pasteurized samples was assessed as follows:

|  | Sample 1 | Sample 2 | Sample 2 | Sample 4 | Sample 5 |
|---|---|---|---|---|---|
| Factor IX ($\mu$/ml) | 1.8 | 1.1 | 0.7 | 0.8 | 0 |
| Volume (ml) | 9.1 | 8.0 | 8.6 | 7.6 | 1.8 |
| Total Factor IX Units | 16.4 | 8.8 | 6 | 6 | 0 |
| % Recovery | 82.4 | 30.9 | 26 | 29 | 0 |
| % Retained Clotting Activity (Over Unpasteurized sample) | 75 | 40 | 27 | 27 | 0 |

What is claimed is:

1. A method for the heat stabilization of a plasma protein comprising heating the protein in an aqueous medium in the presence of ammonium or potassium citrate in an amount in excess of 2.0 M to saturation of the aqueous medium.

2. A method for the pasteurization of a plasma concentrate of a plasma protein comprising pasteurizing the plasma concentrate in the presence of ammonium or potassium citrate in an amount of from in excess of 2.0 M to saturation of the concentrate.

3. A method for the preparation of a pasteurized plasma concentrate of C1-INA or Factor IX comprising partially purifying a C1-INA or Factor IX plasma fraction, concentrating the partially purified product, and pasteurizing the resultant concentrate in the presence of ammonium or potassium citrate in an amount of from in excess of 2.0 M to saturation of the concentrate.

4. The method of claim 3, wherein the plasma fraction is partially purified by ion-exchange chromatography and precipitation with polyethylene glycol.

5. The method of claim 1, wherein the citrate is present in an amount in excess of about 2.5 M.

6. The method of claim 2, wherein the citrate is present in an amount in excess of 2.5 M.

7. The method of claim 3, wherein the citrate is present in an amount in excess of 2.5 M.

8. The methods of claims 1, 2, 3, 4, 5, 6, or 7, wherein the citrate is ammonium citrate.

9. The methods of claims 1, 2, 3, 4, 5, 6, or 7, wherein the citrate is potassium citrate.

10. The methods of claims 1, 2, 3, 4, 5, 6, or 7, wherein the medium or concentrate has a pH of about neutral.

* * * * *